US007445902B2

(12) United States Patent
Briggs et al.

(10) Patent No.: US 7,445,902 B2
(45) Date of Patent: Nov. 4, 2008

(54) FLUORESCENT NUCLEOTIDE ANALOGUES

(75) Inventors: Mark Samuel Briggs, Cardiff (GB);
John Anthony Smith, Cardiff (GB);
Albert Francis Santos, Cardiff (GB)

(73) Assignee: GE Healthcare UK Limited, Amersham (GB)

( * ) Notice: Subject to any disclaimer, the term of this patent is extended or adjusted under 35 U.S.C. 154(b) by 16 days.

(21) Appl. No.: 11/576,353

(22) PCT Filed: Sep. 27, 2005

(86) PCT No.: PCT/GB2005/003685

§ 371 (c)(1),
(2), (4) Date: Apr. 24, 2007

(87) PCT Pub. No.: WO2006/035207

PCT Pub. Date: Apr. 6, 2006

(65) Prior Publication Data
US 2007/0287162 A1    Dec. 13, 2007

(30) Foreign Application Priority Data
Sep. 30, 2004  (GB) ................. 0421691.7
Jan. 12, 2005  (GB) ................. 0500504.6

(51) Int. Cl.
C12Q 1/68    (2006.01)
G01N 33/53   (2006.01)
C07G 3/00    (2006.01)
C07H 19/04   (2006.01)
(52) U.S. Cl. .............. 435/6; 435/7.1; 435/7.2; 536/4.1; 536/26.6
(58) Field of Classification Search .............. 435/6, 435/7.1, 7.2; 536/4.1, 26.6
See application file for complete search history.

(56) References Cited
U.S. PATENT DOCUMENTS

| 5,268,486 | A  | 12/1993 | Waggoner et al. |
| 6,323,186 | B1 | 11/2001 | Klaubert et al. |
| 6,573,374 | B1 | 6/2003  | Muehlegger et al. |
| 2003/0186348 | A1 | 10/2003 | Thomas et al. |

FOREIGN PATENT DOCUMENTS

| EP | 1042407      | 12/2001 |
| WO | WO02/26891   | 4/2002  |
| WO | WO02/086088  | 10/2002 |
| WO | WO2005/024380| 3/2005  |
| WO | WO2006/035208| 4/2006  |

OTHER PUBLICATIONS

Anonymous. (2004). Jena Bioscience Product Catalog: XP-002369683. (Online), retrieved Feb. 24, 2006 from http://www.jenabioscience.com/index.php/8e86af4e8f099e545bc047e0ee40a6bc/1/browse/345>.

Arai, Y., Sugawa, M., Iwane, A. H. & Yanagida, T. (Aug. 2004). "Dynamic polymorphism of a cellular signal protein Ras studied by single molecule FRET: How does Ras interact with many effectors to regulate signaling pathways?" XP-002369620. Abstracts of Papers American Chemical Society, 228(2), U206. & Abstract. (2004). [228th Meeting of the Division of Chemical Toxicology of the American Chemical Society, held Aug. 22-26, 2004, Philadelphia, PA]. ISSN: 0065-7727.

Adhikari, A. & Sprang, S. R. (Dec. 19, 2003). "Thermodynamic Characterization of the Binding of Activator of G Protein Signaling 3 (AGS3) and Peptides Derived from AGS3 with Gαi1*". The Journal of Biological Chemistry, 278(51), 51825-51832. & Chemical Abstract. (2005). ACS Online CAPLUS Abstract No. 140:195104. American Chemical Society on STN.

Cunliffe, J., Liu, Z., Pawliszyn, J. & Kennedy, R. (2004). "Use of a native ligand for the detection of G proteins by capillary isoelectric focusing with laser-induced fluorescence detection". Electrophoresis, 25(14), 2319-2325. & Chemical Abstract. (2005). ACS Online CAPLUS Abstract No. 141:327911. American Chemical Society on STN.

Draganescu, A., Hodawadekar, S. C., Gee, K. R. & Brenner, C. (2000). "Fhit-nucleotide Specificity Probed with Novel Fluorescent and Fluorogenic Substrates*". The Journal of Biological Chemistry, 275(7), 4555-4560. & Chemical Abstract. (2005). ACS Online CAPLUS Abstract No. 132:305036. American Chemical Society on STN.

Gellibolian, R. & Rouhani, R. (2005). Chemical Abstract. "Assaying transferase activity by using an artificial, multifunctional substrate comprising small-molecule component linked to biopolymer-substrate-mimetic component". ACS Online CAPLUS Abstract Accession No. 2005:239208. American Chemical Society on STN.

Jameson, E. E., Cunliffe, J. M., Neubig, R. R., Sunahara, R. K. & Kennedy, R. T. (Aug. 15, 2003). "Detection of G Proteins by Affinity Probe Capillary Electrophoresis Using a Fluorescently Labeled GTP Analogue". Analytical Chemistry, 75(16), 4297-4304. & Chemical Abstract. (2005). ACS Online CAPLUS Abstract No. 139-226677. American Chemical Society on STN.

Klaubert, D. H., Gee, K. R. & Brenner, C. M. (2005). Chemical Abstract. "Phosphate-bound polyazaindacene derivatives of nucleotides". ACS Online CAPLUS Abstract No. 136:2485. American Chemical Society on STN.

McEwen, D. P., Gee, K. R., Kang, H. C. & Neubig, R. R. (2001). "Fluorescent BODIPY-GTP Analogs: Real-Time Measurement of Nucelotide Binding to G Proteins". Analytical Biochemistry, 291(1), 109-117. & Chemical Abstract. (2005). ACS Online CAPLUS Abstract No. 135:58010. American Chemical Society on STN.

Muehlegger, K., Hoeltke, H. Birkner, C. & Eltz, H. V. (2005). Chemical Abstract. "Preparation of infrared dye-marked nucleotides for marking, detection, and sequencing of nucleic acids". ACS Online CAPLUS Abstract No. 123:286528. American Chemical Society on STN.

(Continued)

Primary Examiner—Jezia Riley
(74) Attorney, Agent, or Firm—Yonggang Ji

(57) ABSTRACT

The present invention provides fluorescent cyanine dye-based nucleotide analogues, in which the cyanine dye is coupled to the γ-phosphate group of a nucleoside triphosphate. Preferred embodiments of the invention are directed to fluorescent cyanine dye-based GTP analogues which may be employed in an homogeneous FRET-based assay to measure the binding of guanine nucleotides to GPCR polypeptides, or alternatively, to measure the effect of an exogenous ligand on GPCR protein binding.

21 Claims, No Drawings

OTHER PUBLICATIONS

Ramachandran, S. & Cerione, R. A. (2004). "Stabilization of an Intermediate Activation State for Transducin by a Fluorescent GTP Analogue". Biochemistry, 43(27), 8778-8786. & Chemical Abstract. (2005). ACS Online CAPLUS Abstract No. 141:169674. American Chemical Society on STN.

Whelan, R., Sunahara, R. K., Neubig, R. R. & Kennedy, R. T. (2004). "Affinity Assays Using Fluorescence Anisotropy with Capillary Electrophoresis Separation". Analytical Chemistry, 76(24), 7380-7386. & Chemical Abstract. (2005). ACS Online CAPLUS Abstract No. 142:109770. American Chemical Society on STN.

Williams, J. G. K. (2005). Chemical Abstract. "DNA polymerase mutants with increase activity for charge-switch nucloetides". ACS Online CAPLUS Abstract No. 137:347515. American Chemical Society on STN.

US 7,445,902 B2

FLUORESCENT NUCLEOTIDE ANALOGUES

CROSS REFERENCE TO RELATED APPLICATIONS

This application is a filing under 35 U.S.C. § 371 and claims priority to international patent application number PCT/GB2005/003685 filed Sep. 27, 2005, published on Apr. 6, 2006, as WO 2006/035207, which claims priority to patent application numbers 0421691.7 filed in Great Britain on Sep. 30, 2004 and 0500504.6 filed in Great Britain on Jan. 12, 2005; the disclosures of which are incorporated herein by reference in their entireties.

FIELD OF INVENTION

The present invention relates to fluorescent dye-substituted nucleotides useful in protein binding assays. In particular, the invention relates to fluorescent cyanine dye-based GTP analogues.

BACKGROUND OF THE INVENTION

G-protein coupled receptors (GPCRs) are important targets for drug discovery since they are involved in a wide range of cellular signalling pathways and are implicated in many pathological conditions, such as cardiovascular and mental disorders, cancer and AIDS. Agonist binding to GPCRs facilitates guanine nucleotide exchange in G-proteins by catalysing the release of GDP from the α-subunit of the heterotrimeric GTP binding proteins (G-proteins) and allowing the binding of GTP which activates the G-proteins (Milligan, G., Trends in Pharm. Sci., (2003), 24, No 2, 87-90).

There is a continuing desire within the pharmaceutical industry to exploit GPCRs and orphan GPCRs as drug targets. Many methods have been used to measure GPCR activity and in vitro assays form an important part of high throughput screening strategies in the search for new GPCR-active ligands. Recently, there has been a desire to move towards sensitive, non-radioactive, and in particular homogeneous screening assays for GPCRs. A robust signal, in particular an optical signal that can be easily measured on a spectrophotometer, is an advantage. Thus, fluorescently-labelled non-hydrolysable GTP analogues have been developed for screening assays for GPCR-active ligands. U.S. Pat. No. 6,323,186 (Klaubert et al) relates to dipyrromethene-boron difluoride-substituted nucleotides in which the dipyrromethene-boron difluoride label is attached to a phosphate group of the nucleotide. McEwen et al (Analytical Biochemistry, (2001), 291, 109-117) synthesised three BODIPY GTPγS analogues (FL, 515, and TR), BODIPY FL GppNHp and BODIPY FL GTP compounds to study guanine nucleotide binding. There were reported variances in both fluorescence output as well as binding affinities compared to reference compounds, GTPγS and GppNHp upon binding to Gα$_o$, with some analogues showing significant fluorescence increase upon binding. It was also shown that binding affinities also varied depending on the Gα subtype under study. In a separate study, Gille et al (Naunyn-Schmeideberg's Arch. Pharmacol., (2003), 368, 210-215), showed that BODIPY-FL-guanosine 5'-[γ-thio] triphosphate (B-GTPγS) and BODIPY-FL-guanosine 5'-[β,γ-imido]triphosphate (B-GppNHp) induced fluorescence changes upon binding to purified Gs/Gi-proteins and were suggested as probes for monitoring receptor-mediated G-protein activation. However, in the expression systems employed, these analogues were found to bind to receptor-Gα$_s$/Gα$_i$ fusion proteins with 1,100-5,600-fold and 17-55- fold lower affinity than GTPγS and GppNHp, respectively. Their conclusion was that the steric bulk of the BODIPY group strongly reduces the affinity of GTPγS/GppNHp analogues for G-proteins.

An homogeneous GTP binding assay for G-protein coupled receptors based on time resolved FRET has previously been described (Frang, H., et al GTP binding assay for GPCRs based on TR-FRET, Poster PO 8123, Ninth Annual Society for Biomolecular Screening, Portland, Oreg., 21-25 September 2003). In this assay a biotinylated BioKey® peptide is employed that recognizes only the GTP bound form of the Gα subunit. The biotinylated peptide enables binding of streptavidin-europium in close proximity to an acceptor-labelled GTP, which is also bound to the Gα subunit. FRET occurs as a result of interaction between the streptavidin-europium (donor) and the fluorescently labelled GTP analogue (Alexa647-GTP).

A patent application entitled "Method for Measuring Binding of a Test Compound to a G-Protein Coupled Receptor" (Amersham Biosciences UK Limited) and filed on Sep. 30, 2004 as GB 0421693.3, now published as international application WO2006/035208, discloses a method for measuring test compound binding to a G-protein coupled receptor by means of fluorescence resonance energy transfer (FRET). FRET is a distance-related process in which the electronic excited states of two dye molecules interact without emission of a photon. See, Forster, T., "Intermolecular Energy Transfer and Fluorescence", Ann. Physik., Vol. 2, p. 55, (1948). One result of this interaction is that excitation of a donor molecule enhances the fluorescence emission of an acceptor molecule and the fluorescence quantum yield of the donor is correspondingly diminished. By "donor", it is meant that the dye moiety is capable of absorbing energy from light and emits light at wavelength frequencies which are at least partly within the absorption spectrum of the acceptor. By "acceptor", it is meant that the dye moiety is capable of absorbing energy at a wavelength emitted by a donor dye moiety. For FRET to occur, suitably, the donor and acceptor dye molecules must be in close proximity (typically between 10-100 Å), since energy transfer efficiency decreases inversely as the 6th power of the distance (r) between the donor and acceptor molecules.

While a variety of fluorescent dye-nucleotide conjugates are available, the selection of a particular fluorescent label for use in a protein binding assay can be problematic, since the electronic and spatial requirements of the binding site of the protein of interest are difficult to predict a priori. There is therefore, still a requirement for new fluorescent GTP analogues that may be used for quantitating G-proteins and for studying the kinetics of agonist induced guanine nucleotide exchange in in vitro assays and in cellular systems.

SUMMARY OF THE INVENTION

The present invention provides fluorescent cyanine dye-based nucleotide analogues, in which the cyanine dye is coupled to the γ-phosphate group of a nucleoside triphosphate. Preferred embodiments of the invention are directed to fluorescent cyanine dye-based GTP analogues which may be employed in an homogeneous FRET-based assay to measure the binding of guanine nucleotides to GPCR polypeptides, or alternatively, to measure the effect of an exogenous ligand on GPCR protein binding.

DETAILED DESCRIPTION OF THE INVENTION

The present inventors have discovered that a cyanine dye may be coupled to the γ-phosphate group of a nucleoside triphosphate via a linking group of from 1 to 20 atoms and that the resultant dye-nucleotide conjugate can be a suitable acceptor in a FRET-based assay for G-proteins. Accordingly, in one aspect, the present invention provides a fluorescently labelled reporter compound comprising a cyanine dye covalently linked to the γ-phosphate of a nucleoside 5'-triphosphate.

The reporter is suitably a compound of formula (I):

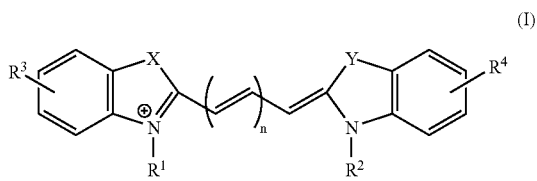

(I)

wherein:
X and Y are the same or different and are selected from >C(CH$_3$)$_2$, —O— and —S—;
one of groups R$^1$, R$^2$, R$^3$ and R$^4$ is the group W where W is:

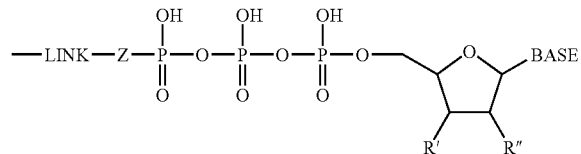

wherein:
BASE is a purine or pyrimidine base;
R' and R" are independently H or OH;
Z is —O—, —S—, or —NR$^5$—, where R$^5$ is H or C$_1$-C$_4$ alkyl;
LINK is a linking group containing from 1-20 linked carbon atoms which may optionally include one or more groups selected from —NR$^5$—, —O—, —C(O)— and —CO—NR$^5$—, where R$^5$ is hereinbefore defined; and
when any of groups R$^1$ and R$^2$ is not said group W, said remaining groups R$^1$ and R$^2$ are independently selected from H and C$_1$-C$_4$ alkyl, which may be optionally substituted with sulphonic acid or sulphonate;
when any of groups R$^3$ and R$^4$ is not said group W, said remaining groups R$^3$ and R$^4$ are independently selected from H, sulphonic acid and sulphonate; and
n is an integer from 1 to 3;

and biologically compatible salts thereof.

Alternatively, the reporter may comprise a rigidized trimethine cyanine dye moiety, the reporter having the general structure (II):

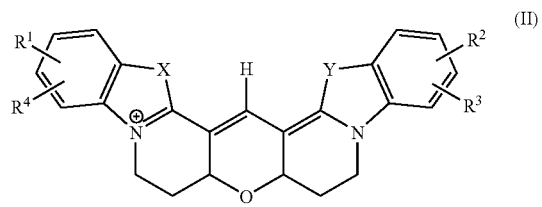

(II)

wherein:
X and Y are the same or different and are selected from >C(CH$_3$)$_2$, —O— and —S—;
one of groups R$^1$, R$^2$, R$^3$ and R$^4$ is the group W where W is hereinbefore defined; and
remaining groups R$^1$, R$^2$, R$^3$ and R$^4$ are selected from H, sulphonic acid and sulphonate; and biologically compatible salts thereof.

Suitably, BASE is a purine or pyrimidine base and is selected from adenine, guanine, hypoxanthine, xanthine, thymine, uracil and cytosine. Preferably, BASE is a purine base selected from a guanine and an adenine base moiety. Particularly preferred is guanine. Structures of the preferred BASE moieties are shown below.

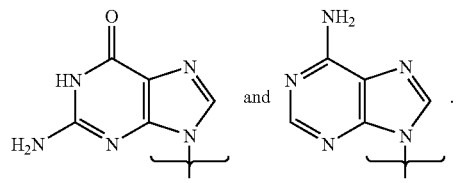

Suitably, groups R' and R" are selected independently from hydroxyl or hydrogen. Thus, the sugar moiety may be a ribose-sugar (R'=R"=OH, a 2'- or 3'-deoxyribose-sugar (R'≠R") or a 2',3'-dideoxyribose-sugar (R'=R"=H). Preferably, R' and R" are both OH.

Suitably, the linking group "LINK" is a group for covalent attachment of the cyanine dye to the γ-phosphate group of the nucleotide through group Z. Suitably, LINK contains from 1-20 linked carbon atoms which may optionally include one or more groups selected from —NR$^5$—, —O—, —C(O)— and —CO—NR$^5$—, where R$^5$ is selected from hydrogen and C$_1$-C$_4$ alkyl. The linking moiety may include part of the substituents extending from the cyanine dye chromophore. Thus, the linking moiety is attached to the dye chromophore but is not a part of it. Suitable linkers are selected from the group consisting of alkyl chains containing from 1 to 20 carbon atoms which may optionally include from 1 to 4 oxygen atoms as polyether linkages, or from 1 to 4 nitrogen atoms as secondary or tertiary amine linkages, or up to two —CO—NH— groups as polyamide linkages.

In the above formulae, Z is an atom or group of two or more atoms suitable for covalently attaching the γ-phosphate group of the nucleotide to the linking group "LINK". Suitably, Z is selected from —O—, —S—, or —NR$^5$—, where R$^5$ is H or C$_1$-C$_4$ alkyl. In preferred embodiments, Z is —O—, or —NH—. The group —NH— is to be particularly preferred, since the amino-phosphate attachment group serves to confer additional stability to the dye-nucleotide analogue, thereby rendering the compound more resistant to enzymatic attack.

In a preferred embodiment, the compounds of formula (I) have the formula (III):

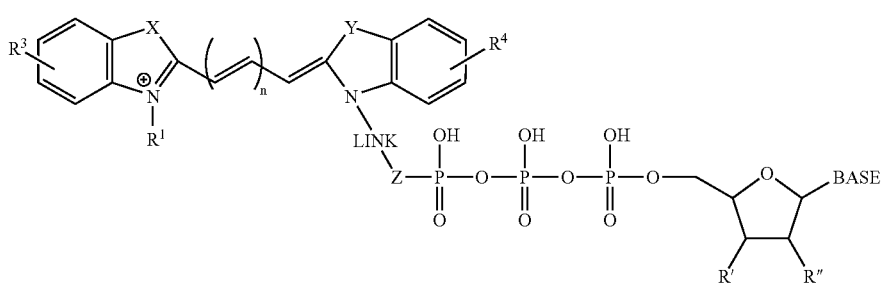

(III)

wherein:
R[1] is $C_1$-$C_4$ alkyl, which may be optionally substituted with sulphonic acid or sulphonate;
R[3] and R[4] are independently selected from H, sulphonic acid and sulphonate;
BASE is selected from a guanine and an adenine base; and
X, Y, LINK, Z, R', R" and n are hereinbefore defined; and biologically compatible salts thereof.

In this embodiment, LINK is preferably the group: —$(CH_2)_p$-Q-$(CH_2)_m$—, where Q is selected from: —$CH_2$— and —CO—NH—; p is 1-10 and m is 2-6. In particularly preferred embodiments according to the invention, LINK is selected from the groups: —$(CH_2)_5$—CO—NH—$(CH_2)_2$— and —$(CH_2)_5$—CO—NH—$(CH_2)_6$—.

The preferred cyanine dye moieties are particularly useful, due to the wide range of structural variations and spectral properties available that may be obtained by varying the number of carbon atoms in the methine bridge. It is possible to synthesise dyes having particular excitation wavelengths to correspond to a particular excitation source, such as a laser, e.g. a HeNe laser or a diode laser. In the preferred compounds according to the present invention, the number of methine groups linking the heterocyclic ring systems containing X and Y defines the absorption maxima of the cyanine dye moiety. Thus, the absorption maxima increase from Cy™3 (n=1) to Cy5 (n=2) to Cy7 (n=3) by an increment of approximately 100 nm each as illustrated in Table 1 below. The corresponding emission peaks of Cy3, Cy5 and Cy7 are also separated by approximately 100 nm, as shown in Table 1. Thus, the fluorescence emission of the fluorescent dye nucleotide conjugate may be chosen to suit the application. For avoidance of background interference in a biological assay, it is preferable to employ a fluorescent dye moiety having an emission wavelength above about 650 nm. Thus, dye nucleotide reporter compounds of the present invention useful for protein binding assays will preferably include a Cy5 dye component where n=2.

TABLE 1

| Compound | Structure X = Y = $C(CH_3)_2$ | Abs max (nm) | Em max (nm) |
|---|---|---|---|
| Cy3 | n = 1 | 550 | 570 |
| Cy5 | n = 2 | 649 | 670 |
| Cy7 | n = 3 | 743 | 767 |

The cyanine dye moiety may be substituted at the X and Y position independently by >$C(CH_3)_2$, —O— and —S—. In a preferred embodiment, X and Y are the same and are >$C(CH_3)_2$.

Preferably, at least one of the groups R[1], R[2], R[3] and R[4] of the cyanine dye moiety may include water solubilising constituents attached thereto, suitably sulphonic acid or sulphonate groups. Useful examples of solubilising constituents attached at the R[1] and R[2] positions of formula (I) are —$(CH_2)_3$ $SO_3^-$ and —$(CH_2)_4$—$SO_3^-$. However, one or more sulphonic acid or sulphonate groups attached directly to the aromatic ring structures of the cyanine dye moiety of formulas (I) and (II) are particularly preferred.

Suitably, the compounds of formulas (I) and (II) may include one or more counter-ions which may be positive or negative to balance the formal charge (or charges) on the molecule. The nature of the counter-ion is not material to the invention and could be one of many known ions such as $NH_4^+$, $NHEt_3^+$, $K^+$, $Li^+$, $Na^+$, acetate ($H_3CCO_2^-$), $PO_4^{3-}$, $HPO_4^{2-}$, $Cl^-$, $Br^-$, or $I^-$. When the compounds of the present invention are employed in enzyme assays or in protein binding assays, it is preferable that any counter-ions that are present should not interfere with the assay under study, i.e. any counter-ion should be non-toxic and be biologically compatible. Thus, particularly preferred counter-ions are selected from $NH_4^+$, $NHEt_3^+$, $Na^+$, $PO_4^{3-}$ and $Cl^-$.

In particularly preferred embodiments, the cyanine dye-nucleotide reporter compound has the formula (IV):

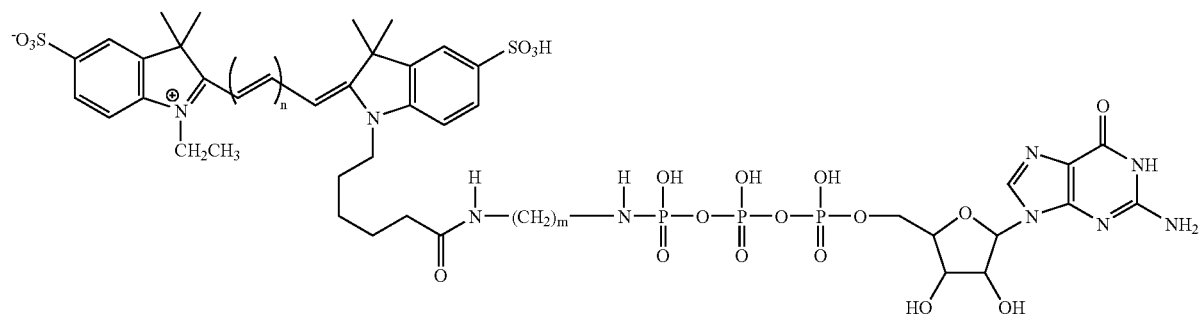

(IV)

wherein:
n is 1, 2 or 3, preferably 2; and
m is 2 to 6.

Useful examples of compounds according to the invention that are particularly suitable for use in G-protein binding assays and for measuring binding of ligands to a G-protein coupled receptor are as follows:

(Clinical Chemistry, (2002), 48(8), 1352-59), to form a diaminoalkyl-modified GTP. In the second stage of the procedure, an amino-reactive cyanine dye derivative is allowed to react with the ω-amino group of the nucleotide analogue to form the fluorescent cyanine dye-labelled derivative. Purification of the product may be carried out by HPLC using a weak anion exchange resin such as DEAE and eluting with a

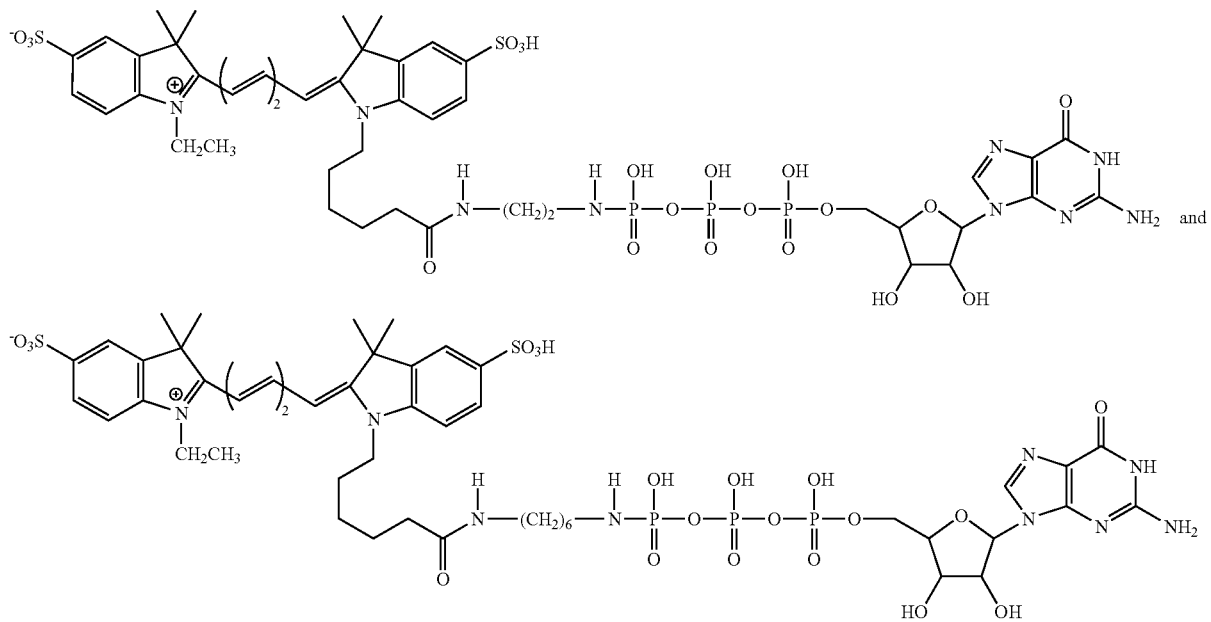

and

Compounds of formula (I) and (II) are suitably prepared by a process comprising reacting together:
(a) a nucleoside triphosphate analogue having the formula:

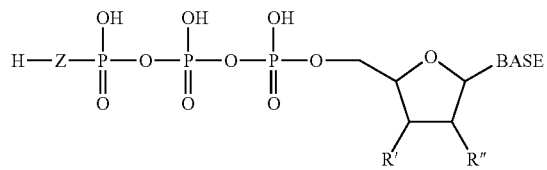

wherein BASE, R', R" and Z are hereinbefore defined;
(b) a cyanine dye derivative having a reactive substituent suitable for covalent bonding with a nucleophilic functional group such as HO—, HS—, or HNR$^5$—, where R$^5$ is H or $C_1$-$C_4$ alkyl; and
(c) optionally, a third component suitable for forming a linkage between components a) and b), said third component being a bi-functional linking moiety, for example having the formula:

in which A and B are independently a nucleophilic functional group selected from HO—, HS—, or HNR$^5$—, where R$^5$ is H or $C_1$-$C_4$ alkyl, and m is an integer from 2 to 10; either in a single step or a multiple step process to form the reporter compounds of the invention. For example, 5'-GTP may be reacted with an α,ω-diaminoalkane in the presence of imidazole and N-(3-dimethylaminopropyl)-N'-ethylcarbodiimide (EDC) by a method analogous to that of van Gijlswijk et al salt gradient such as sodium chloride. The required compound may be de-salted by further HPLC purification using reverse phase resin and eluted with a gradient of triethylammonium acetate or bicarbonate solution into acetonitrile. After collection of the required compound, excess triethylammonium salt may be removed by lyophilisation.

Suitably, according to the process of the invention, compounds of formula (I) may be prepared from a cyanine dye derivative having the formula:

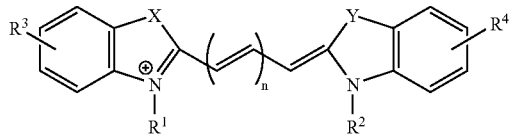

wherein at least one of groups $R^1$, $R^2$, $R^3$ and $R^4$ contains or is modified to contain said reactive substituent; and X, Y and n are hereinbefore defined. Cyanine dyes having a reactive substituent suitable for covalent linkage to a nucleophilic HO—, HS—, or HNR$^5$— group may be prepared according to known methods; see, for example, Waggoner, A. S. et al, Cytometry, (1990), 11, 418-430; Waggoner, A. S. et al, Bioconjugate Chemistry, (1993), 4(2), 105-111; U.S. Pat. No. 5,268,486 (Waggoner, A. S. et al).

Alternative cyanine dye derivatives for use in the process are the rigidized trimethine cyanine dyes disclosed in EP 1042407 B1 (Waggoner, A. S. et al). The rigidized trimethine dyes have the following general structure:

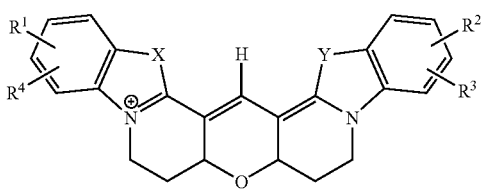

wherein at least one of groups $R^1$, $R^2$, $R^3$ and $R^4$ contains or is modified to contain said reactive substituent; and X and Y are hereinbefore defined.

The compounds of the present invention may be used in an homogeneous FRET-based assay to measure the binding of guanine nucleotides to GPCR polypeptides, for example G-proteins, or alternatively, to measure the effect of an exogenous ligand on GPCR protein binding, in which the GPCR polypeptide comprises a Gα subunit comprising a covalently bound tag and a GTP binding site. The method comprises the steps of: i) contacting the Gα subunit with a fluorescent GTPase resistant GTP analogue according to the present invention, wherein said analogue comprises a first fluorescence resonance energy transfer (FRET) label; ii) contacting the Gα subunit with a detection molecule that comprises a binding moiety that specifically binds to the covalently bound tag and a second FRET label; and iii) measuring the fluorescence intensity resulting from the intramolecular interaction between the first and second FRET labels in the presence and absence of a potential ligand; wherein an increase in fluorescence intensity indicates and is a measure of the potency of ligand binding to the GPCR polypeptide. Compounds of the present invention may additionally be used in an homogeneous method to measure the effect of an agent or an environment on modulating the binding of a ligand to a GPCR polypeptide. The method as hereinbefore described is performed in the presence of the agent and the binding compared with that in the absence of the agent, wherein any change in the binding in the presence and absence of the agent is indicative of a modulator of ligand binding.

Suitably, the covalently bound tag and the binding moiety are members of a specific binding pair, and may be selected from the group consisting of biotin/streptavidin, biotin/avidin, antigen/antibody, GST/glutathione, His tag/Nickel, FLAG/M1 antibody, maltose binding protein/maltose, chitin binding protein/chitin and calmodulin binding protein/calmodulin (Terpe, Appl. Microbiol. Biotechnol., (2003), 60, 523-533). Preferably, the tag is biotin and the binding moiety is either streptavidin or avidin labelled with the second FRET label which can act as the FRET donor.

Suitably, in the method described above, the GTPase-resistant GTP analogue is a reporter compound having the formula (I) according to the present invention, preferably having a Cy5 dye component where n=2. Suitably, the FRET donor dye is a xanthene dye or a cyanine dye, preferably a cyanine dye, for example Cy3B. Other suitable donor labels can include europium or terbium chelates.

In a typical example, the assay method employs a fully constitutive GPCR and associated G-proteins, including an integral Gα-biotin G-protein subunit. The procedure may be performed in black 96-well microwell plates. A reference ligand is added to appropriate wells at a suitable final concentration range (typically 1-100 nM) in assay binding buffer. Into the same wells is added either zero agent (buffer only) or agent at increasing concentrations (10 μl) (typically, but not restricted to, a range of 1 nM-10 μM). The selected wells of the microwell plate will also contain excess non-labelled GTPγS (10 μl) (typically, but not restricted to, 100 μM; 10 μM final) to assess the degree of non-specific binding (NSB). Membranes containing fully reconstituted GPCR of interest with associated G-proteins, part of which will consist of biotin-tagged Gα subunit (10 μl) (typically 1-4 pmoles/well) is added. This is followed by the FRET donor component, for example Cy3B-streptavidin (10 μl) (typically 20 nM final; 2 pmols/well) and the FRET acceptor component, for example, compound (IV) (n=2; m=2 or 6) (10 μl) (typically 40 nM final; 4 pmol/well). The volume of the wells is made up to 100 μl with assay buffer as appropriate. Suitably, the assay buffer employed is 20 mM HEPES, 3 mM $MgCl_2$, 100 mM NaCl+ 100 μg/ml saponin, pH 7.5. Other buffers can include TRIS, with varying concentrations of $MgCl_2$, NaCl and detergents. Following agitation of the assay mix on a plate shaker for approx. 45 minutes at room temperature, an increase in the fluorescence of the acceptor dye may be detected using a fluorescence plate detector, with filter settings at 531 nm (excitation, bandwidth 25 nm) and 665 nm (emission, bandwidth 7.5 nm).

EXAMPLES

The invention is illustrated by reference to the following examples. The present examples are provided for illustrative purposes only, and should not be interpreted in any way as limiting the scope of the invention as defined by the appended claims. All references provided below and elsewhere in the present specification are hereby included herein via reference.

1. Synthesis of Cy5 Labelled GTP Analogue:
Cy5-C2-GTP (Compound 1)

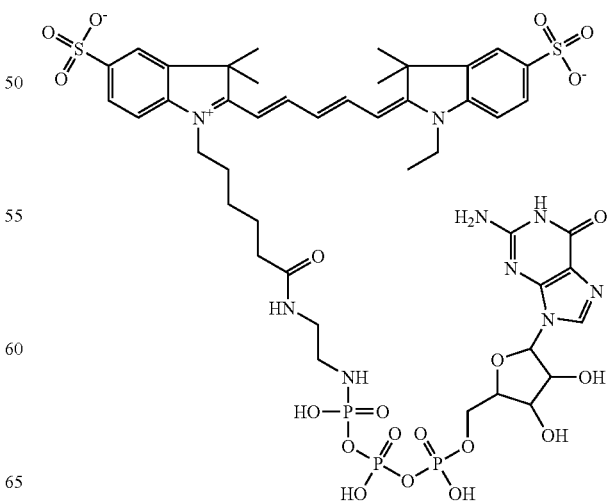

1.1 Synthesis of O$^{5'}$-[3-(2-aminoethylamino)-1,2,3-trihydroxy-triphosphoryl-quanosine: Compound 2

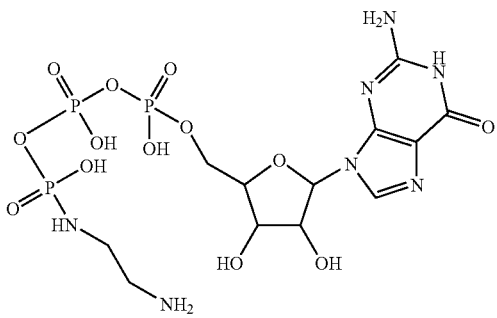

The tetra-lithium salt of GTP (25 mg, 0.048 mmol) and N-(3-dimethylaminopropyl)-N'-ethylcarbodiimide hydrochloride (36 mg, 0.190 mmol) were dissolved in 4 ml of 0.1M triethanolamine hydrochloride buffer (pH 7.2) in a 25 ml round-bottomed flask fitted with a magnetic stirrer bead. N-Fmoc-ethane-1,2-diamine hydrobromide (113 mg, 0.31 mmol) was suspended in 1.5 ml of 1,4-dioxan and added to the stirred solution in the flask. DMF was added dropwise to the suspension in the flask until it became homogeneous. The solution was stirred at ambient temperature under an atmosphere of nitrogen for 20 hours. TLC (RP-18, 40:60 methanol:water) showed that all the GTP had reacted. The solution was evaporated to dryness under vacuum. 2.5 ml of a mixture of 20:80 piperidine:DMF was added to the residue and the mixture stirred at ambient temperature for 15 minutes. The solution was then evaporated to dryness under vacuum. The residue was dissolved in water (10 ml) and extracted with diethyl ether (2×10 ml), the aqueous phase was then evaporated to dryness under vacuum. TLC (RP-18, 40:60 methanol:water) showed a single spot ($R_f$ 0.75) which turned purple when sprayed with ninhydrin.

The residue was dissolved in water and purified by HPLC using a MonoQ™ 10/10 column (Amersham Biosciences) eluting with a gradient of water to 100% 0.5M triethylammonium acetate solution (pH 7.0) over 60 minutes at a flow of 3 ml/minute. Detection was at 260 nm. The major product eluted after 36 minutes. This material was evaporated to dryness under vacuum and the residue dissolved in a minimal volume of water. This was further purified by reverse phase HPLC using a 250×10 mm Jupiter™ C-18 column (Phenomenex) eluting with 0.1M triethylammonium acetate solution (pH 7.0) at a flow of 4 ml/minute. Detection was at 260 nm. A single peak eluted after 11.3 minutes. This material was evaporated to dryness under vacuum, the residue was dissolved in water and the process repeated several times to remove as much triethylammonium acetate as possible to give Compound 2 as a colourless solid.

Mass spectrometry (ES$^+$) gave MH$^+$ at 566 and MNa$^+$ at 588. ($C_{12}H_{22}N_7O_{13}P_3$ requires 565.3)

Calculated yield from absorption at 253 nm was 7.1 mg (0.012 mmol, 25%)

1.2 Synthesis of Cy5 Labelled GTP Analogue: Cy5-C2-GTP (Compound 1)

Compound 2 (2 µmol) was dissolved in 0.2 ml of water in a 1.5 ml polypropylene V-vial. To this was added 100 µl 0.1 M sodium bicarbonate solution followed by 200 µl of a solution of 10 mg (14.4 µmol) Cy5-NHS ester in 1 ml dry DMSO. The tube was placed on rollers for 20 hours at ambient temperature. This material was purified by reverse phase HPLC using a 250×10 mm Jupiter C-18 column (Phenomenex) eluting with a gradient of 0.1 M triethylammonium acetate solution (pH 7.0) to 50% acetonitrile over 30 minutes at a flow of 4 ml/minute. Detection was at 650 nm. The component eluting after 20 minutes was collected, then evaporated to dryness under vacuum to give Compound 1 as a blue solid.

Mass spectrometry (ES$^+$) gave MNa$^{2+}$ at 614.7 and MNa$^+$ at 1228.3 ($C_{45}H_{60}N_9O_{20}P_3S_2$ requires 1203)

Calculated yield from absorption at 649 nm was 0.56 mg (0.46 µmol, 23%)

2. Synthesis of Cy5 Labelled GTP Analogue: Cy5-C6-GTP (Compound 3)

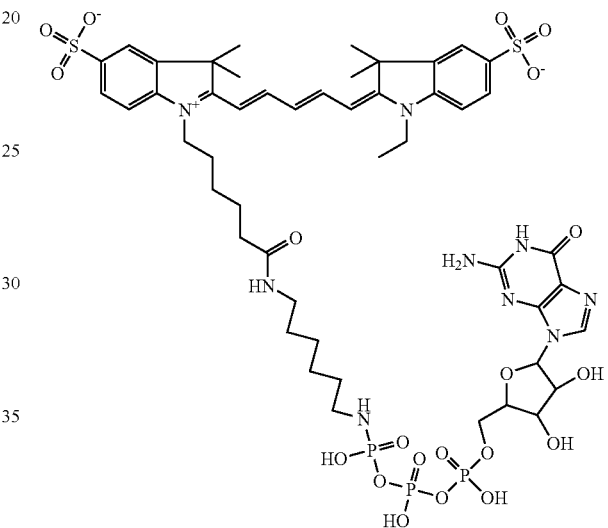

2.1 Synthesis of O$^{5'}$-[3-(6-aminohexylamino)-1,2,3-trihydroxy-trihosphoryl-quanosine: Compound 4

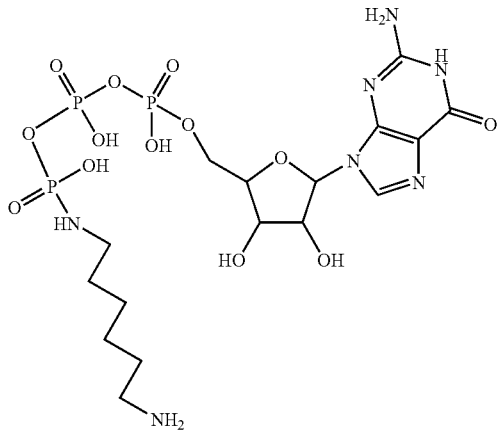

The tetra-lithium salt of GTP (25 mg, 0.048 mmol) was dissolved in 2 ml of 0.1M triethanolamine hydrochloride buffer (pH 7.2) in a 25 ml round-bottomed flask fitted with a magnetic stirrer bead. To this was added N-Fmoc-hexane-1,6-diamine hydrobromide (42 mg, 0.10 mmol) dissolved in 1 ml dry DMF. N-(3-dimethylaminopropyl)-N'-ethylcarbodiimide hydrochloride (72 mg, 0.37 mmol) was dissolved in 1 ml of the triethanolamine buffer and added to the stirred solution in the flask. DMF was added dropwise to the suspension in the flask until it became homogeneous. The solution was stirred at ambient temperature under an atmosphere of nitrogen for 20 hours. TLC (RP-18, 40:60 methanol:water) showed that some of the GTP had still not reacted. A further portion of N-(3-dimethylaminopropyl)-N'-ethylcarbodiimide hydrochloride (72 mg, 0.37 mmol) was added and stirring was continued for a further 20 hours. The solution was evaporated to dryness under vacuum. 5 ml of a mixture of 20:80 piperidine:DMF was added to the residue and the mixture stirred at ambient temperature for 15 minutes. The solution was then evaporated to dryness under vacuum.

The residue was dissolved in water (10 ml) and extracted with diethyl ether (2×10 ml), the aqueous phase was then evaporated to dryness under vacuum. TLC (RP-18, 40:60 methanol:water) showed a single spot ($R_f$ 0.75) which turned purple when sprayed with ninhydrin. The residue was dissolved in water and purified by HPLC using a MonoQ 10/10 column (Amersham Biosciences) eluting with a gradient of water to 100% 0.5 M triethylammonium acetate solution (pH 7.0) over 60 minutes at a flow of 3 ml/minute. Detection was at 260 nm. The major product eluted after 22 minutes. This material was evaporated to dryness under vacuum and the residue dissolved in a minimal volume of water. This was further purified by reverse phase HPLC using a 250×10 mm Jupiter C-18 column (Phenomenex) eluting with a gradient of 0.1 M triethylammonium acetate solution (pH 7.0) to 40% acetonitrile over 40 minutes at a flow of 4 ml/minute. Detection was at 260 nm. A single peak eluted after 25 minutes. This material was evaporated to dryness under vacuum, the residue dissolved in water and the process repeated several times to remove as much triethylammonium acetate as possible to give Compound 4 as a colourless solid.

Mass spectrometry (ES$^+$) gave MH$^+$ at 622.21. ($C_{16}H_{30}N_7O_{13}P_3$ requires 621.1)

Calculated yield from absorption at 253 nm was 3.5 mg (0.007 mmol, 15%)

2.2 Synthesis of Cy5 Labelled GTP Analogue: Cy5-C6-GTP (Compound 3)

Compound 4 (2.3 μmol) was dissolved in 0.2 ml of water in a 1.5 ml polypropylene V-vial. To this was added 200 μl 0.1 M sodium bicarbonate solution followed by 300 μl of a solution of 10 mg (14.4 μmol) Cy5-NHS ester in 1 ml dry DMSO. The tube was placed on roller for 20 hours at ambient temperature. The material was purified by ion exchange HPLC (Hiprep™ 16/10 DEAE FF column). The column was eluted with water from 0-9 minutes, then water to 35% 2 M sodium chloride from 9-40 minutes at a flow rate of 5 ml/minute. Detection was at 253 and 650 nm. The major product eluted after 28 minutes. This material was de-salted by reverse phase HPLC using a 250×10 mm Jupiter C-18 column (Phenomenex) eluting with 0.1M triethylammonium acetate solution (pH 7.0) at a flow of 4 ml/minute. Detection was at 253 and 650 nm. The major component was collected then evaporated to dryness under vacuum to give Compound 3 as a blue solid.

Mass spectrometry (ES$^+$) gave MH$^+$ at 1260.3. ($C_{49}H_{67}N_9O_{20}P_3S_2$ requires 1258.3)

Calculated yield from absorption at 649 nm was 0.7 mg (0.6 μmol, 26%)

3. Synthesis of Cy3B Labelled GTP Analogue: Cy3B-C2-GTP (Compound 5)

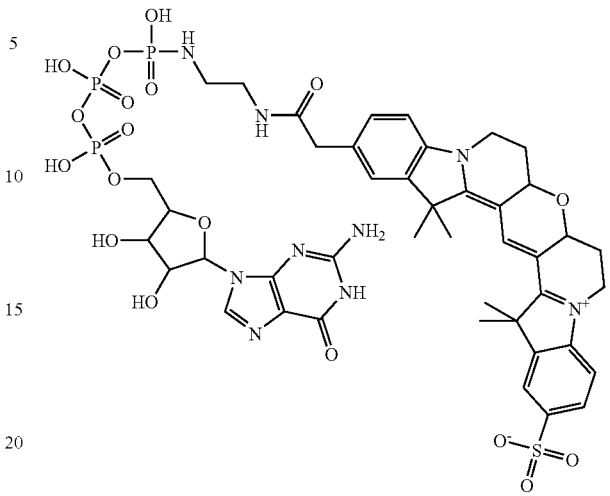

Dowex 50 W-X8 (H$^+$ form) was converted to the pyridinium form by washing with pyridine/water, then water. The tetra-lithium salt of GTP (25 mg, 0.05 mmol) was dissolved in the minimal volume of water and passed through the column to convert it to the pyridinium salt. This material was dried under vacuum, then converted into the tri-n-butylammonium salt by co-evaporation with tri-n-butylamine and dry DMF. This material was then dissolved in dry DMSO (1 ml), then pyridine hydrochloride (8 mg) was added followed by dicyclohexylcarbodiimide (60 mg, 0.33 mmol). The solution was stirred magnetically for 16 hours at ambient temperature. N-Fmoc-ethane-1,2-diamine hydrobromide (40 mg, 0.11 mmol) was added, followed by diisopropylethylamine (20 μl) and stirring continued for a further 20 hours. The solvent was removed under vacuum and the residue stirred with 1 ml of 20:80 piperidine:DMF for 40 minutes.

The solvent was removed under vacuum, then water (50 ml) was added and the precipitate filtered off. As much solvent as possible was removed under vacuum leaving a turbid solution. This was filtered through a 0.45 μm Millipore filter before purification by ion exchange HPLC using a MonoQ 10/10 column (Amersham Biosciences) eluting with a gradient of water to 100% 0.5M triethylammonium acetate solution (pH 7.0) over 60 minutes at a flow of 4 ml/minute. Detection was at 260 nm. Material eluting after 30 minutes was collected and evaporated to dryness under vacuum to leave a sticky, white residue. This was dissolved in 1 ml of dry DMSO in a 1.5 ml polypropylene V-vial. To this was added 40 μl of diisopropylethylamine followed by 500 μl of a solution of 9 mg (11.7 μmol) Cy3B-NHS ester in 1 ml dry DMSO. The tube was placed on rollers for 7 hours at ambient temperature. The material was purified by reverse phase HPLC using a 250×10 mm Jupiter C-18 column (Phenomenex) eluting with 0.1 M triethylammonium acetate solution (pH 7.0) to 70% acetonitrile over 30 minutes at a flow of 4 ml/minute. Detection was at 550 nm. A component eluting after 12 minutes was collected, then evaporated to dryness under vacuum to give Compound 5 as a red solid.

Mass spectrometry (ES$^+$) gave MH$^{2+}$ at 554.6 and MH$^+$ at 1108. ($C_{43}H_{52}N_9O_{18}P_3S$ requires 1107)

Calculated yield from absorption at 550 nm was 4.7 mg (4.3 μmol, 9%)

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

The invention claimed is:

1. In a method for a homogeneous fluorescence resonance energy transfer (FRET) assay for measuring binding of a ligand to a GPCR polypeptide, which method comprises the steps of:
   i) contacting the GPCR polypeptide, which contains a Gα subunit comprising a covalently bound tag and a GTP binding site, with a fluorescent GTPase resistant GTP analogue, wherein said analogue comprises a first fluorescence resonance energy transfer (FRET) label;
   ii) contacting the GPCR with a detection molecule that comprises a binding moiety that specifically binds to the covalently bound tag and a second FRET label; and
   measuring the fluorescence intensity resulting from the intramolecular interaction between the first and second FRET labels in the presence and absence of said ligand;
wherein an increase in fluorescence intensity is a measure of the potency of ligand binding to the GPCR polypeptide;
the improvement comprises: using a compound having the formula hereinbelow as a donor or an acceptor of the FRET assay:

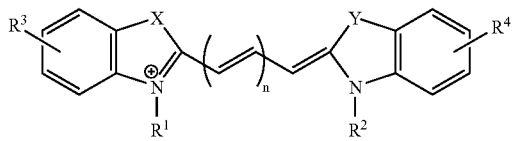

wherein:
   X and Y are the same or different and are selected from >C(CH$_3$)$_2$, —O— and —S—;
   one of groups R$^1$, R$^2$, R$^3$ and R$^4$ is the group W where W is:

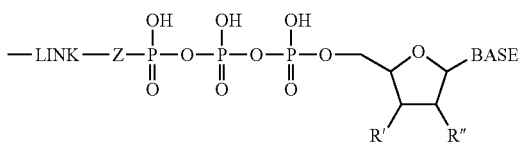

wherein:
   BASE is a purine base;
   R' and R" are independently H or OH;
   Z is —O—, —S—, or —NR$^5$—, where R$^5$ is H or C$_1$-C$_4$ alkyl;
   LiNK is a linking group containing from 1-20 linked carbon atoms which may optionally include one or more groups selected from —NR$^5$—, —O—, —C(O)— and —CO—NR$^5$—, where R$^5$ is hereinbefore defined; and
   when any of groups R$^1$ and R$^2$ is not said group W, said remaining groups R$^1$ and R$^2$ are independently selected from H and C$_1$-C$_4$ alkyl, which may be optionally substituted with sulphonic acid or sulphonate;
   when any of groups R$^3$ and R$^4$ is not said group W, said remaining groups R$^3$ and R$^4$ are independently selected from H, sulphonic acid and sulphonate; and
   n is an integer from 1 to 3;
   and biologically compatible salts thereof.

2. In a method for a homogeneous fluorescence resonance energy transfer (FRET) assay for measuring binding of a ligand to a GPCR polypeptide, which method comprises the steps of:
   (i contacting the GPCR polypeptide, which contains a Gα subunit comprising a covalently bound tag and a GTP binding site, with a fluorescent GTPase resistant GTP analogue, wherein said analogue comprises a first fluorescence resonance energy transfer (FRET) label;
   ii) contacting the GPCR with a detection molecule that comprises a binding moiety that specifically binds to the covalently bound tag and a second FRET label; and
   iii) measuring the fluorescence intensity resulting from the intramolecular interaction between the first and second FRET labels in the presence and absence of said ligand;
   wherein an increase in fluorescence intensity is a measure of the potency of ligand binding to the GPCR polypeptide;
   the improvement comprises: using a compound having the formula hereinbelow as a donor or an acceptor of the FRET assay:

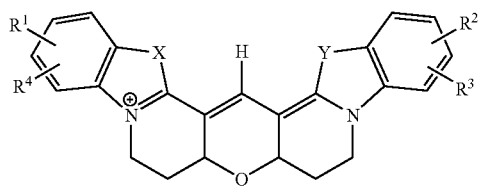

wherein:
   X and Y are the same or different and are selected from >C(CH$_3$)$_2$, —O— and —S—; one of groups R$^1$, R$^2$, R$^3$ and R$^4$ is the group W where W is:

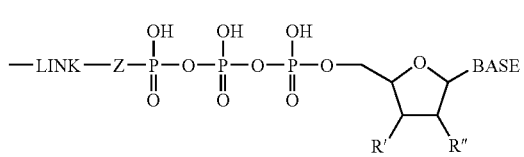

wherein:
   BASE is a purine base;
   R' and R" are independently H or OH;
   Z is —O—, —S—, or NR$^5$—, where R$^5$ is H or C$_1$-C$_4$ alkyl;
   LiNK is a liniking group containing from 1-20 linked carbon atoms which may optionally include one or more groups selected from —NR$^5$—, —O—, —C(O)— and —CO—NR$^5$—, where R$^5$ is hereinbefore defined;
   remaining groups R$^1$, R$^2$, R$^3$ and R$^4$ are selected from H, sulphonic acid and sulphonate; and biologically compatible salts thereof.

3. The method of claim 1, wherein the compound is of the formula:

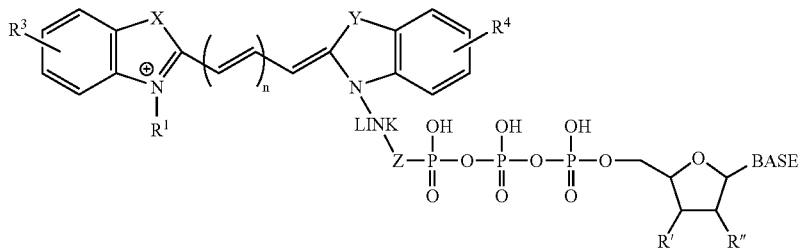

wherein:
R$^1$ is C$_1$-C$_4$ alkyl, which may be optionally substituted with sulphonic acid or sulphonate;
R$^3$ and R$^4$ are independently selected from H, sulphonic acid and sulphonate;
BASE is a guanine base; and
X, Y, LiNK, Z, R', R" and n are hereinbefore defined; and biologically compatible salts thereof.

4. The method of claim 1, wherein BASE is a guanine.

5. The method of claim 4, wherein BASE has the structure:

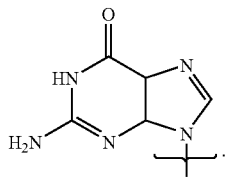

6. The method of claim 1, wherein R' and R" are OH.

7. The method of claim 1, wherein LiNK is the group: —(CH$_2$)$_p$-Q-(CH$_2$)$_m$—, where Q is selected from: —CH$_2$— and —CO—NH—; p is 1-10 and m is 2-6.

8. The method of claim 7, wherein LINK is selected from the groups: —(CH$_2$)$_5$—CO—NH—(CH$_2$)$_2$- and —(CH$_2$)$_5$—CO—NH—(CH$_2$)$_6$—.

9. The method of claim 1, wherein Z is —O—, or —NR$^5$—.

10. The method of claim 9, wherein Z is —NH—.

11. The method of claim 1, wherein X and Y are the same and are >C(CH$_3$)$_2$.

12. The method of claim 1, wherein the compound has the formula:

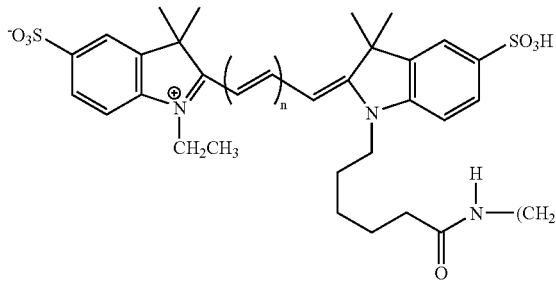 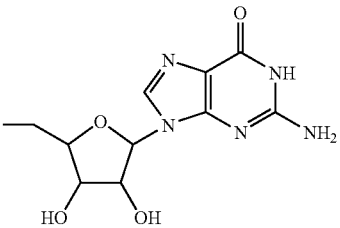

wherein:
n is 1,2 or 3; and
m is 2 to 6;
and biologically compatible salts thereof.

13. The method of claim 1, wherein the compound is selected from:

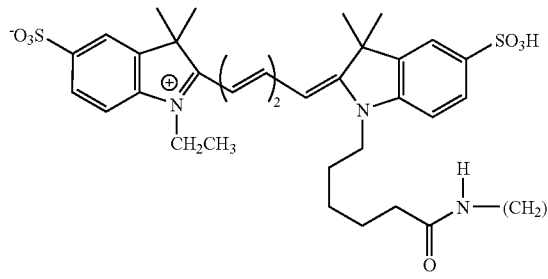 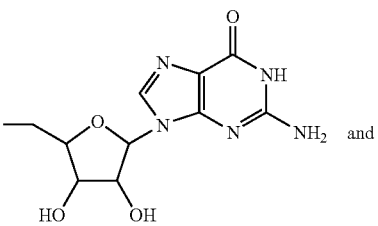 and

-continued

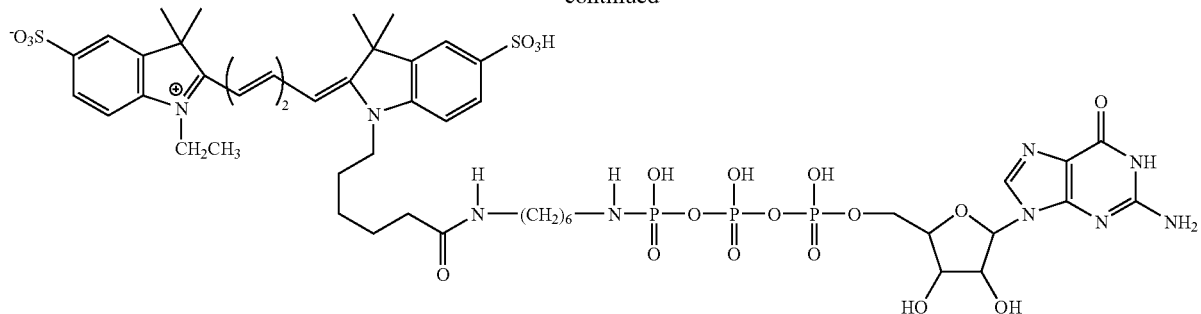

and biologically compatible salts thereof.

14. The method of claim 2, wherein BASE is a guanine.

15. The method of claim 14, wherein BASE has the structure:

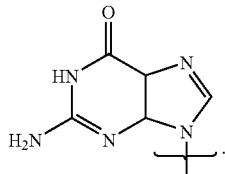

16. The method of claim 2, wherein R' and R" are OH.

17. The method of claim 2, wherein LiNK is the group: $-(CH_2)_p-Q-(CH_2)_m-$, where Q is selected from: $-CH_2-$ and $-CO-NH-$; p is 110 and m is 2-6.

18. The method of claim 17, wherein LiNK is selected from the groups: $-(CH_2)_5-CO-NH-(CH_2)_2-$ and $-(CH_2)_5-CO-NH-(CH_2)_6-$.

19. The method of claim 2, wherein Z is $-O-$, or $-NR^5-$.

20. The method of claim 19, wherein Z is $-NH-$.

21. The method of claim 2, wherein X and Y are the same and are $>C(CH_3)_2$.

* * * * *